(12) United States Patent
Weiss et al.

(10) Patent No.: US 6,179,839 B1
(45) Date of Patent: Jan. 30, 2001

(54) BONE FUSION APPARATUS AND METHOD

(75) Inventors: Arnold-Peter Weiss, Barrington, RI (US); Michael S. Collins, San Diego, CA (US)

(73) Assignee: Kinetikos Medical Incorporated, San Diego, CA (US)

( * ) Notice: Under 35 U.S.C. 154(b), the term of this patent shall be extended for 0 days.

(21) Appl. No.: 09/399,021

(22) Filed: Sep. 20, 1999

(51) Int. Cl.[7] ................................................. A61B 17/80
(52) U.S. Cl. ............................. 606/69; 606/77; 606/80; 606/85
(58) Field of Search ................................ 606/69, 70, 79, 606/80, 81, 85, 91, 71, 84; 623/22.15, 22.21, 22.36, 22.35

(56) References Cited

U.S. PATENT DOCUMENTS

| | | | |
|---|---|---|---|
| 3,939,497 | * | 2/1976 | Heimke et al. . |
| 5,314,490 | * | 5/1994 | Wagner et al. ......................... 623/22 |
| 5,919,195 | * | 7/1999 | Wilson et al. ......................... 606/80 |

* cited by examiner

Primary Examiner—Michael Buiz
Assistant Examiner—David O. Reip
(74) Attorney, Agent, or Firm—Jenkins & Wilson, P.A.

(57) ABSTRACT

A bone fusion apparatus and method for positioning over and attachment to a desired bone area which can provide for radial compression of bones, with particular suitability for wrist fusion by attachment to suitable bones such as, for example, a plurality of carpus area bones, with or without attachment to the radius bone and/or to one or more metacarpal bones. The bone fusion apparatus includes an annular plate having an outer side for at least partially contacting bone and an opposite inner side. The plate has a top outer edge of greatest diameter and a smaller diameter, bottom inner edge which defines an at least substantially central opening through the plate. The plate is substantially conical in shape such that the plate tapers outwardly from the inner edge of the plate to the outer edge of the plate. The plate defines a plurality of preferably countersunk holes therethrough between the inner edge and the outer edge, wherein each of the holes is adapted for receiving a bone fastener. Also provided is a bone burr and handle which can easily be utilized to precisely burr bone at a location where the bone fusion apparatus is to be placed in order for the bone fusion apparatus to precisely be positioned and affixed to bone as desired.

19 Claims, 7 Drawing Sheets

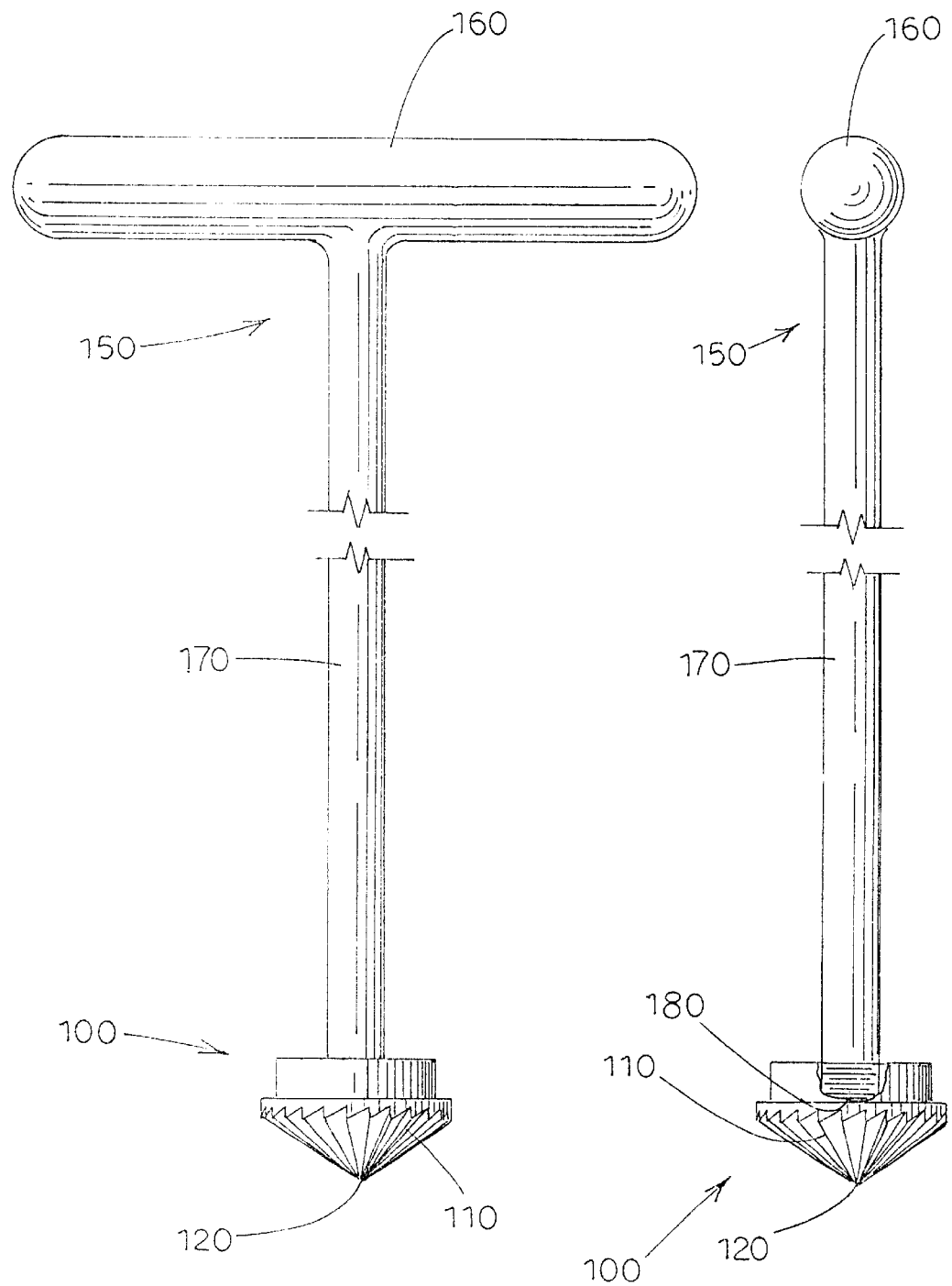

BONE FUSION APPARATUS AND METHOD

TECHNICAL FIELD

The present invention relates generally to orthopaedic bone apparatuses and methods, and more particularly, to an anatomical bone fusion apparatus and method which can be utilized for bone fusion in a variety of orthopaedic settings, such as, for example, for wrist bone fusion.

BACKGROUND ART

As can be appreciated by those of skill in the art of orthopaedic apparatuses and methods, it is common to utilize a bone fusion plate for attaching to bones at a desired location to position the bones relative to one another wherein bones beneath the plate can be fused together. To accomplish such bone fusion, bone plates which have commonly been used to date are typically flat along a single plane and include holes for attachment of bone fasteners, such as bone screws, to bones below. This type of attachment of a bone plate to the bones below typically provides vertical compression only between the bones and the bone plate above and does not provide for any kind of radial or lateral compression which can urge the bones toward one another and which is highly advantageous in bone fusion.

Bone plates suffering the above-mentioned disadvantages exist in a variety of configurations and can be adapted for use at various anatomical locations, such as, for example, with wrist bones, foot bones, cranial-facial bones, and bones at any other location suitable for bone fusion. For use specifically with wrists, it is common for a wrist fusion apparatus such as a wrist fusion plate to be used in arthrodesis to fuse bones of the wrist area of a patient in a desired orientation. A variety of configurations and designs of fusion plates specifically for use with wrists exist within the prior art for utilization in this manner.

Generally, the use of a dorsal wrist fusion plate is indicated in patients with osteoarthritis or post-traumatic wrist arthritis, conditions involving significant loss of bone substance, and failed partial or limited wrist arthrodesis. Wrist arthrodesis can also be successfully utilized in patients with carpal instability. A fusion plate can be utilized in patients with rheumatoid arthritis, although simpler stabilization techniques are currently fairly predictable. Contraindications to utilizing a wrist fusion plate adapted for fusion in a limited manner as recognized by those of skill in the art include any concomitant disease or deficiency which may compromise the function of the plate.

Some types of wrist fusion apparatuses attach to the radius and extend from there to a metacarpal, such as the third metacarpal, of the hand for utilization in wrist fusion. Wrist fusion apparatuses of this variety are typically fastened both to the radius and to the third metacarpal by bone screws, and wrist fusion apparatuses of this variety also therefore overlie the carpus area and the bones of the carpus area which are positioned between the radius and the metacarpal bones. As known to those of skill in the art, bone grafts can be packed between the radius, the carpus area bones, and the metacarpals after such a wrist fusion plate is in place, and the bone grafts typically will bond with the adjacent bones in order to create a fused bone mass at the wrist joint.

U.S. Pat. No. 5,853,413 to Carter et al. discloses such a wrist fusion apparatus in the form of a plate configured to extend over the carpus area and to position at least one metacarpal relative to the radius. A saddle portion is included in the wrist fusion plate and is placed over the carpus area. A proximal end extends from the saddle portion and is attachable to the radius, while a distal end extends from the saddle portion and is attachable to one of the metacarpals. The proximal end extending from the saddle portion defines a first longitudinal axis, and the distal end extending from the saddle portion defines a second longitudinal axis wherein the first and second longitudinal axes are not actually aligned in a medial-lateral direction.

Wrist fusion plate apparatuses and methods such as that disclosed in Carter et al. require attachment of a portion of the wrist fusion plate to one or more of the metacarpals of the hand as well as to the radius. The resulting bone fusion can be referred to as total wrist fusion and will typically render a person with no ability to flex the subject wrist for abduction or adduction because of the total fusion of the carpal area bones with the radius and one or more metacarpals. In some circumstances, therefore, it can be desirable to fuse bones of the carpus area only without causing fusion to either the radius or to a metacarpal. In such circumstances, the resulting fusion can be referred to as partial or limited wrist fusion as compared to the total wrist fusion created when the radius and a metacarpal are also fused with the carpal bones.

Regardless of whether a bone fusion apparatus for wrist bone fusion or for fusion of other area bones, and regardless of whether a bone fusion apparatus is adapted for limited wrist fusion or for total wrist fusion, slippage or sliding of the bone fusion apparatus is a common problem which can often be encountered during the affixation or fastening of a bone fusion apparatus, especially for affixation of bone fusion apparatuses for limited, wrist bone fusion. As can be readily appreciated by those of skill in the art, the procedure of screwing in the bone screws which are typically used as fasteners for bone fusion apparatuses can be quite difficult to accomplish without some undesirable movement of the bone fusion apparatus itself. Such movement therefore can make it very difficult to precisely position and affix bone fusion apparatuses.

Despite the prior art bone fusion apparatuses and methods, there remains much room for improvement in the art, particularly for a bone fusion apparatus and method which can be used for fusing a variety of bones in a variety of different anatomical locations.

DISCLOSURE OF THE INVENTION

The present invention provides a novel bone fusion apparatus and method for positioning bones in a desired area relative to one another and fusing the bones. The invention can be adapted for use with a variety of different bones in a variety of different anatomical locations for bone fusion. The present invention is also particularly suitable for fusing wrist bones and can be easily utilized by attachment to a variety of wrist bones, such as, for example, the carpus area bones, the radius bone, and/or one or more metacarpal bones.

In accordance with the present invention, the bone fusion apparatus comprises a three dimensional annular plate having an outer side for at least partially contacting bone and an opposite inner side. The plate has a top outer edge of greatest diameter and a smaller diameter, bottom inner edge which defines an at least substantially central opening through the plate. The plate is substantially conical in shape such that the plate tapers outwardly from the inner edge of the plate to the outer edge of the plate. The plate defines a plurality of preferably countersunk holes therethrough between the inner edge and the outer edge, wherein each of the holes is adapted for receiving a bone fastener such as a bone screw for attaching the plate to a plurality of bones, such as, for example, a plurality of carpus area bones.

For limited wrist bone fusion particularly, the bone fusion apparatus can particularly be positioned such that at least one hole is positioned and aligned over each of the lunate, triquetrium, hamate, and capitate bones and attached by bone screws thereto. In this fashion, the bone fusion apparatus of the present invention can be utilized for wrist fusion without attachment to the radius bone or to a metacarpal bone as desired. Alternatively, the bone fusion apparatus can attach to and be used with a variety of bones of the wrist for total or limited wrist bone fusion.

Also provided in accordance with the present invention is a bone burr and differing handles which can easily be advantageously utilized to precisely position the burr bone at a location where the bone fusion apparatus is to be placed in order for the bone fusion apparatus to precisely be positioned and affixed for bone fusion.

It is therefore an object of the present invention to provide a novel bone fusion apparatus and method for affixation with and fusing a variety of different bones.

It is another object of the present invention to provide a bone fusion apparatus and method which can easily be positioned and affixed in a designated location for fusing bones, and which facilitates fusion of bones to which the bone fusion apparatus is attached.

It is a further object of the present invention to provide a bone fusion apparatus and method which is particularly suitable for fusing wrist bones.

Some of the objects of the invention having been stated hereinabove, other objects will become evident as the description proceeds, when taken in connection with the accompanying drawings as best described hereinbelow. These objects are met in whole or in part by the present invention as described hereinbelow.

BRIEF DESCRIPTION OF THE DRAWINGS

FIG. 8A of the drawings is a side elevation view of a T-handle and bone burr assembly according to the present invention;

FIG. 8B of the drawings is another side elevation view of a T-handle and bone burr assembly according to the present invention.

DETAILED DESCRIPTION OF THE INVENTION

Referring now to the various figures of drawings, a bone fusion apparatus generally designated 10 is illustrated and can be used to position bones in a desired area relative to one another and fuse the bones wherein the bones involved can be a variety of bones, such as wrist bones for example. Bone fusion apparatus 10 is suitable for positioning and fusing a variety of bones in a variety of different anatomical locations. For example, bone fusion apparatus 10 can be used for fusing wrist bones, foot bones, cranial-facial bones, or other bones suitable for bone fusion. Bone fusion apparatus 10 is particularly suitable for fusing wrist bones, even in a partial or limited manner as described herein without attachment to the radius bone or to a metacarpal bone. It is envisioned according to this invention of course that bone fusion apparatus 10 can be utilized for wrist fusion by attachment to the radius bone and/or by attachment to one or more metacarpal bones.

For wrist bone fusion particularly in a limited manner, plate P can be attached to a plurality of carpus area bones for utilization in fusing wrist as can be appreciated by those of skill in the art. Partial or limited wrist fusion as used herein, as discussed above and as can be appreciated by those of skill in the art, means fusion of carpus area bones only without fusion, affixation or attachment to the radius or to a metacarpal.

Despite the particular bones with which bone fusion apparatus 10 is envisioned for utilization, bone fusion apparatus 10 in a preferred embodiment comprises an annular, cone-shaped plate P which can be constructed of any suitable material for purposes as taught herein, but in a preferred embodiment is constructed of stainless steel, a bioabsorbable (resorbable) material, or other suitable material of construction as can be appreciated by those of skill in the art. Plate P is suitably anatomically designed and adapted for positioning over any suitable bones for bone fusion. It is envisioned according to the present invention that the particular shape of plate P can vary within the scope of this invention. More specifically, plate P can be of a rounded circular, oval or elliptical or even of any other suitable outermost shape.

Figure 1A:
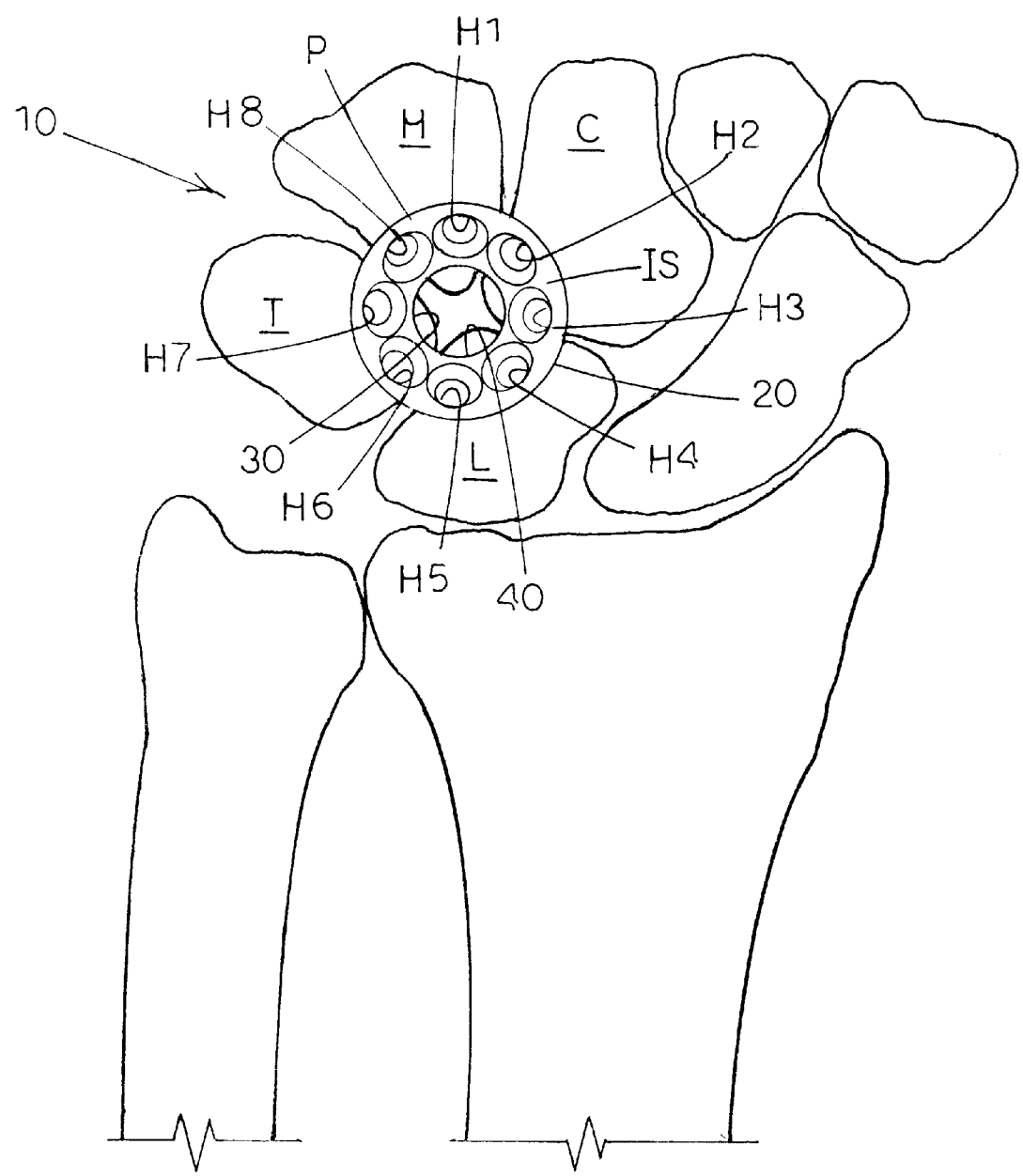
FIG. 1A of the drawings is a top plan view of the bone fusion apparatus according to the present invention in a preferred embodiment shown positioned over a plurality of carpus area bones.

As illustrated in FIG. 1A of the drawings, plate P is shown in a preferred position for utilization in limited wrist bone fusion as plate P is positioned over a plurality of carpus area bones. More specifically, plate P is shown positioned over a plurality of carpus area bones which as shown in FIG. 1A of the drawings comprise a lunate L, a triquetrium T, a hamate H, and a capitate C. While FIG. 1A of the drawings illustrates a preferred position of plate P for utilization in limited wrist fusion, it is specifically envisioned in accordance with this invention that plate P can be positioned over or proximate a radius bone and/or one or more metacarpal bones as desired for any type of wrist fusion as appropriate. Bones of other suitable, non-wrist areas as desirable and as mentioned previously, such as, for example, foot bones or cranial-facial bones, can also be utilized in association with plate P.

Figure 3:
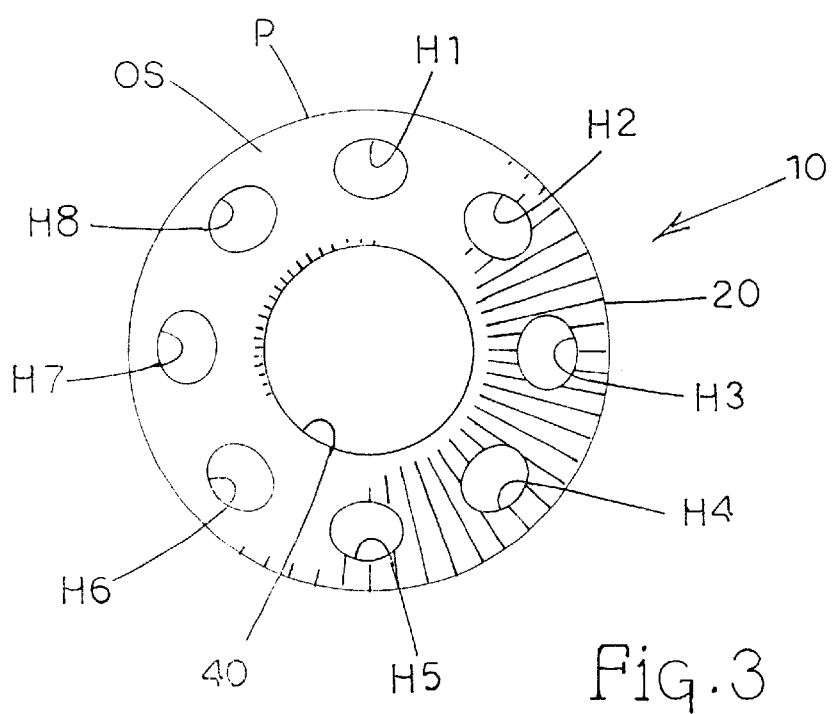
FIG. 3 of the drawings is an isolated bottom plan view of the bone fusion apparatus according to the present invention.
Figure 4:
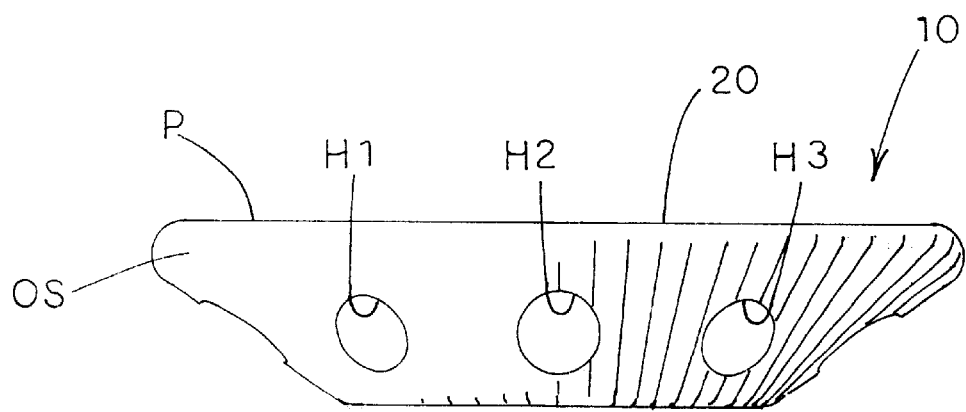
FIG. 4 of the drawings is an elevated side view of the bone fusion apparatus according to the present invention.
Figure 5:
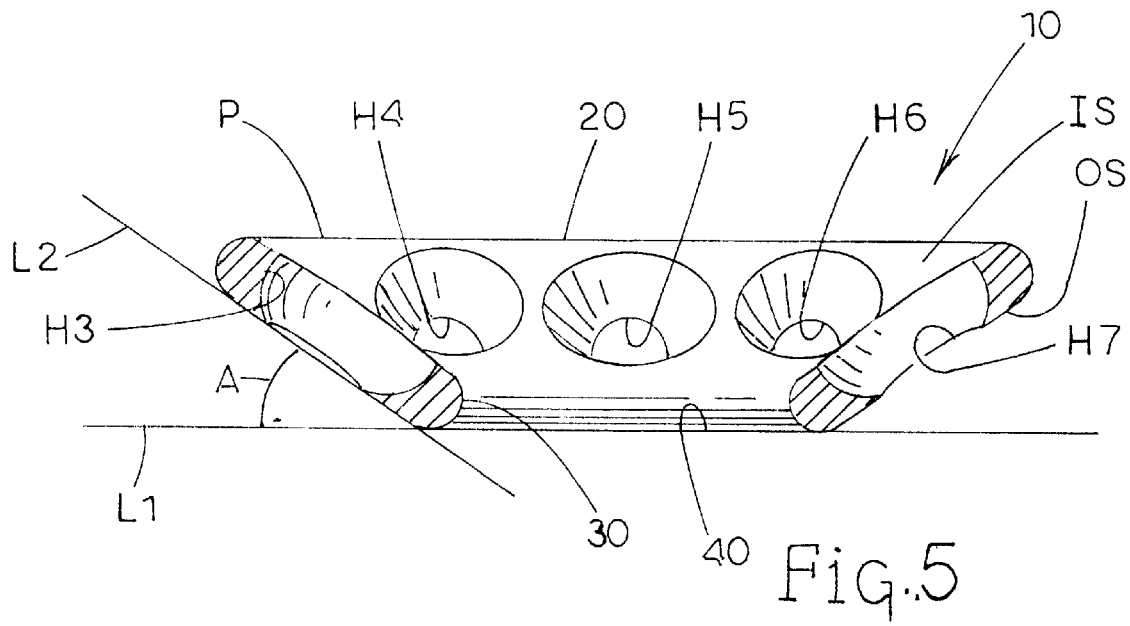
FIG. 5 of the drawings is a cross-sectional view of the bone fusion apparatus according to the present invention drawn along line 5—5 of FIG. 2 of the drawings.
Figure 6:
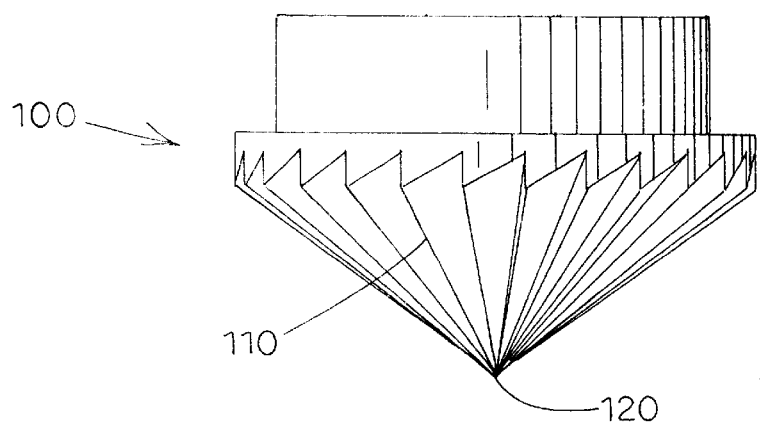
FIG. 6 of the drawings is a side elevation view of a bone burr according to the present invention.

Regardless of the specific location at which bone fusion apparatus 10 is desired for use, annular plate P is preferably at least substantially conical in shape and has an outer side OS, best illustrated in FIGS. 3, 4 and 5, for at least partially contacting bone and an opposite, concave shaped inner side IS, best illustrated in FIGS. 1A, 1B, 2, and 5. Plate P has an outer circumferential edge 20 of greatest diameter and a smaller diameter, inner circumferential edge 30 which defines an at least substantially central opening 40 through plate P. The conical shape of plate P is such that plate P tapers outwardly from inner edge 30 to outer edge 20 wherein plate P defines a plurality of holes therethrough between inner edge 30 and outer edge 20. As shown in the various figures of drawings, the holes are equally spaced-apart and of equal size as a preferred embodiment of plate P comprises holes H1–H8. In the preferred embodiment, holes H1–H8 are countersunk on inner side IS and each hole H1–H8 is adapted for receiving a bone fastener for attaching plate P to a plurality of proximate or underlying bones, such as underlying carpus area bones when involved in limited wrist fusion. Holes H1–H8 therefore are of a larger diameter on inner side IS than on outer side OS of plate P.

As illustrated in the sectional view of FIG. 5 of the drawings, the bottom of plate P defining central opening 40 is disposed along a bottom horizontal plane represented in FIG. 5 as line L1. The conical shaped body of plate P itself is formed at an outer angle A, preferably of between approximately 0 and 90 degrees, to line L1 on all sides of plate P. FIG. 5 shows outer side OS of plate P disposed along line L2 for illustration purposes in its cross-sectional view wherein line L1 and line L2 form angle A on the outer side OS of plate P.

While the dimensions and structure of plate P can suitably vary in accordance with this invention, plate P in a preferred embodiment has a height from central opening 40 to top outer edge 20 of approximately 0.152 inch, a bottom inner edge 30 circumferential width of approximately 0.251 inch, and a top outer edge 20 circumferential width of approximately 0.643 inch.

Referring now to FIGS. 6–9 of the drawings, a bone burr generally designated 100 is provided which can be used for rasping or burring away bone in a precise location where bone fusion apparatus 10 is to be positioned and affixed. Bone burr 100 preferably is at least generally cone-shaped and includes burr teeth 110 on the outside thereon adapted for burring away bone. While it is envisioned according to this invention that bone burr 100 can be constructed of any suitable material for burring away bone, bone burr 100 most preferably is constructed of stainless steel. Bone burr 100 preferably forms a point 120 which is sharp and adapted for burring directly into bone. The size and outer configuration of bone burr 100 at least generally match that of plate P such that bone burr 100 can be easily used to burr away bone in a desired area, such as, for example, the carpus area or another suitable area wherein plate P can subsequently be very easily precisely placed in the burred away location and affixed there in position according to this invention with minimal or no sliding or slipping movement of plate P as it is affixed in position.

Figure 7A:
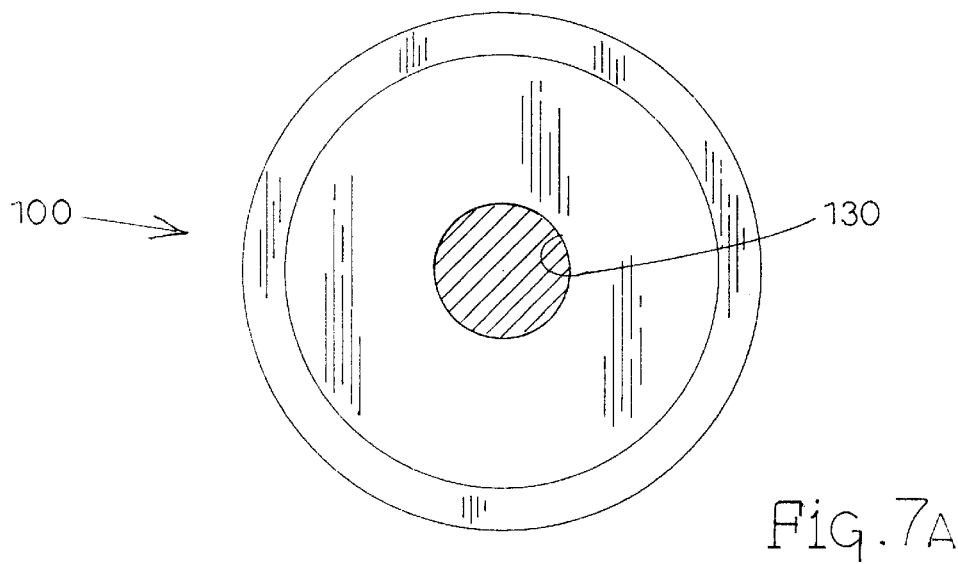
FIG. 7A of the drawings is a top plan view of the bone burr according top the present invention.
Figure 7B:
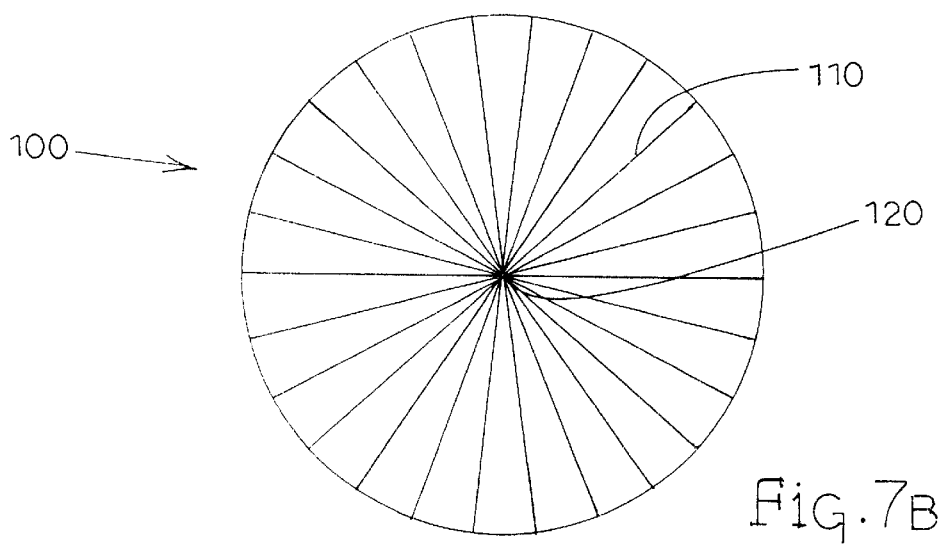
FIG. 7B of the drawings is a bottom plan view of a bone burr according to the present invention.

In its preferred embodiment, bone burr 100 defines a threaded opening 130 in the top center portion of bone burr 100, as best illustrated in FIG. 7A. Opening 130 is adapted for matingly receiving a handle or an attachment or adapter for a power instrument. The handle for manual placement of bone burr 100 can be a "t"-handle generally designated 150, illustrated in FIGS. 8A and 8B of the drawings. "t"-handle 150 is preferably constructed of stainless steel and includes a "t"-shaped handle portion 160 attached perpendicularly to the top of a shaft portion 170. Shaft portion 170 includes a threaded bottom end 180 adapted for matingly engaging with and into opening 130 of bone burr 100 in a secure manner so that rotation of "t"-handle 150 likewise rotates bone burr 100. It is also envisioned according to this invention that "t"-handle 150 and bone burr 100 could be integrally connected and formed as one unit.

Figure 9:
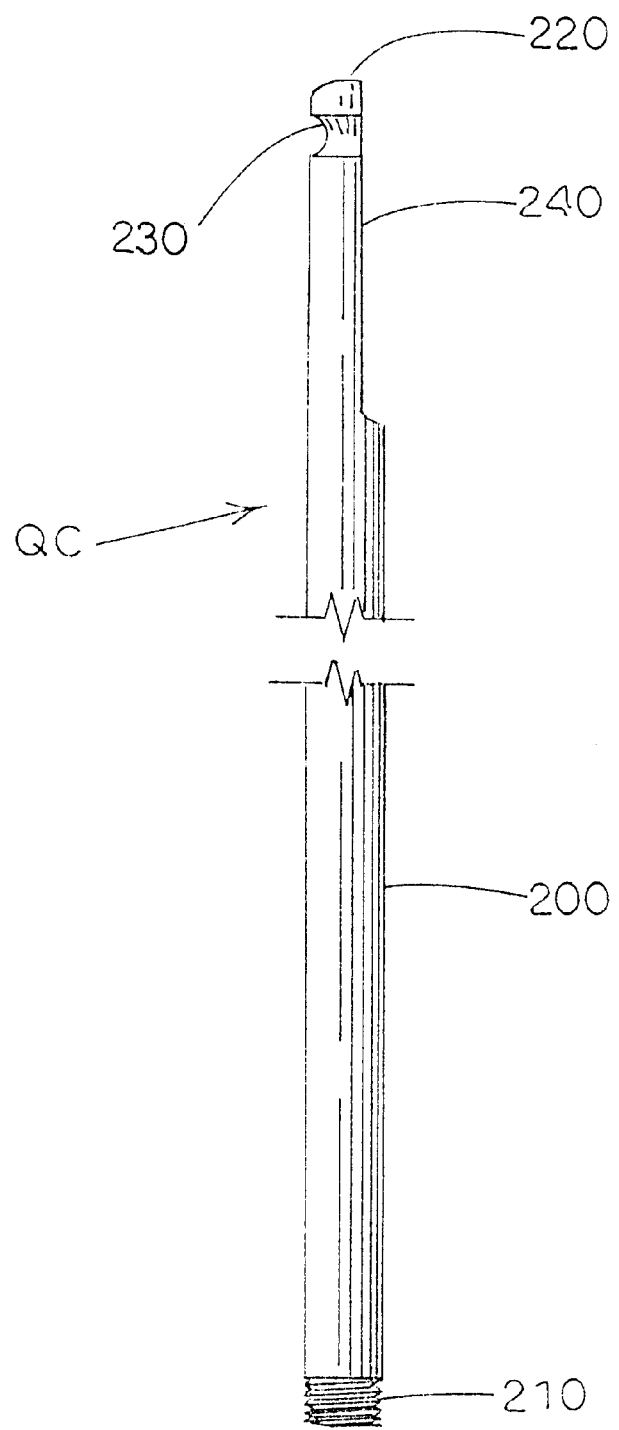
FIG. 9 of the drawings is a side elevation view of an alternative embodiment power instrument adapter which can be used with the bone burr of the present invention.

FIG. 9 of the drawings illustrates the attachment or adapter for a power instrument as quick coupling adapter or device QC is shown. Quick coupling device QC can be of any suitable construction and material and also preferably includes an end which can matingly engage with and into opening 130 of bone burr 100 in a secure manner so that rotation of quick coupling device QC likewise rotates bone burr 100. Quick coupling device QC as shown in a preferred embodiment in FIG. 9 of the drawings comprises an elongated shaft portion 200 with a bottom threaded end 210 for matingly engaging opening 130 of bone burr 100. The opposite end 220 of quick coupling device QC can be adapted for fitting with or into a power instrument such as a drill whereby the power instrument can be used to rotate quick coupling device QC, which in turn can rotate bone burr 100 simultaneously when quick coupling device QC is attached to bone burr 100 by fitting into opening 130. End 220 can be suitably shaped for fitting with or into a power instrument and can in one embodiment as shown in FIG. 9 comprise a notch 230 around outer shaft portion 200. End 220 can also include a flat side portion 240 as shown in FIG. 9.

Bone Positioning and Fusion Method

Bone fusion apparatus 10 according to the present invention and as described above can be utilized effectively and easily for positioning bones in a desired area relative to one another and for bone fusion for a variety of bones in different locations as described herein and as can readily be appreciated by those of skill in the art.

For wrists specifically and as described above, the use of a limited wrist fusion plate is generally indicated in patients with osteoarthritis or post-traumatic wrist arthritis, conditions involving significant loss of bone substance, rheumatoid arthritis, and failed partial wrist arthrodesis. Wrist arthrodesis can also be successfully utilized in patients with carpal instability.

For wrist bone fusion specifically, a preferred method of utilizing bone fusion apparatus 10 can comprise what can be referred to as a method for four-corner limited arthrodesis. After appropriate general or regional block anaesthetic and tourniquet exsanguination of the upper extremity to 250 mm of mercury, a longitudinal incision of approximately 7 cm is made centered over the dorsal wrist. Alternatively, a traverse incision of approximately 6 cm can be utilized. Dissection is carried down through the subcutaneous tissues taking care to protect the sensory branch of the radial and ulnar nerve fibers. In patients who have a SLAC deformity and require scaphoid excision, exposure is undertaken through the third dorsal compartment transposing the extensor pollicis longus tendon radially. The incision is taken from the third compartment between the second and fourth compartments distally through the capsule exposing the scaphoid. The scaphoid can be removed in a piecemeal fashion using a rongeur, taking care to protect the extrinsic ligaments. A radial styloidectomy might be required, and care should be taken to avoid disruption of the extrinsic ligaments with the styloidectomy itself. If desired, exposure to the four-bone region encompassing the lunate, triquetrum, capitate, and hamate can be undertaken through this incision, although it does not require fairly extensive ulnar dissection and can be difficult.

Alternatively, a separate longitudinal incision can be made between the fourth and fifth compartments which provides direct exposure to the four-bone region, and this technique is also utilized in patients who undergo a four-corner fusion for instability alone where the scaphoid does not require excision. After undertaking a longitudinal incision between the fourth and fifth compartments and appropriately exposing the capitate, hamate, lunate, and triquetrum, any instability rotation of any of the four bones is reduced and temporary percutaneous Kirschner wire fixation can be accomplished keeping the K-wires as volar as possible within the four bones.

A small rongeur can be used to denude cartilage between the four bones down through subchrondral bone to good cancellous bone. Bone burr 100 can then be centered over the four bone corner junction, or in any other suitable desired location, and used to burr or rasp bone down flush with the dorsal aspect of the carpus which preferably exactly complements the configuration of the bottom of plate P. This technique allows excellent exposure to good cancellous bone in the four-corner region prior to plate placement. As can be appreciated by those of skill in the art, burring of bone with bone burr 100 can be accomplished by grasping and rotating "t"-handle 150 (or quick connect QC) while forcing it downward. Autogenous cancellous bone graft taken from either the excised scaphoid or Lister's tubercle in the distal radius can then be packed between each of the joint surfaces and in the junction of the four-corner fusion at the bottom of the rasped defect.

After appropriate packing of the bone graft, plate P is then aligned to allow maximum screw placement in each of the four bones. With careful alignment, at least one, and preferably two, screws can be placed within each of the four bones through the fastener holes H1–H8 of plate P. Holding the plate in appropriate alignment, a suitable drill bit, such as a 1.5 mm drill bit, can be used to place one bone screw in each of the four bones. The screws utilized can be of any suitable type and size, and preferably can be 10 mm long or 14 mm long, 2.4 mm diameter cancellous self-tapping screws to fix plate P down in position. The screws are preferably placed in a tightened fashion to allow radial or lateral compression of the bones rather to urge the bones toward one another and desirably facilitate bone fusion. The remaining appropriate fastener holes can be drilled and further screws placed of appropriate length to allow excellent position and yet to avoid protrusion through articular surfaces.

Figure 1B:
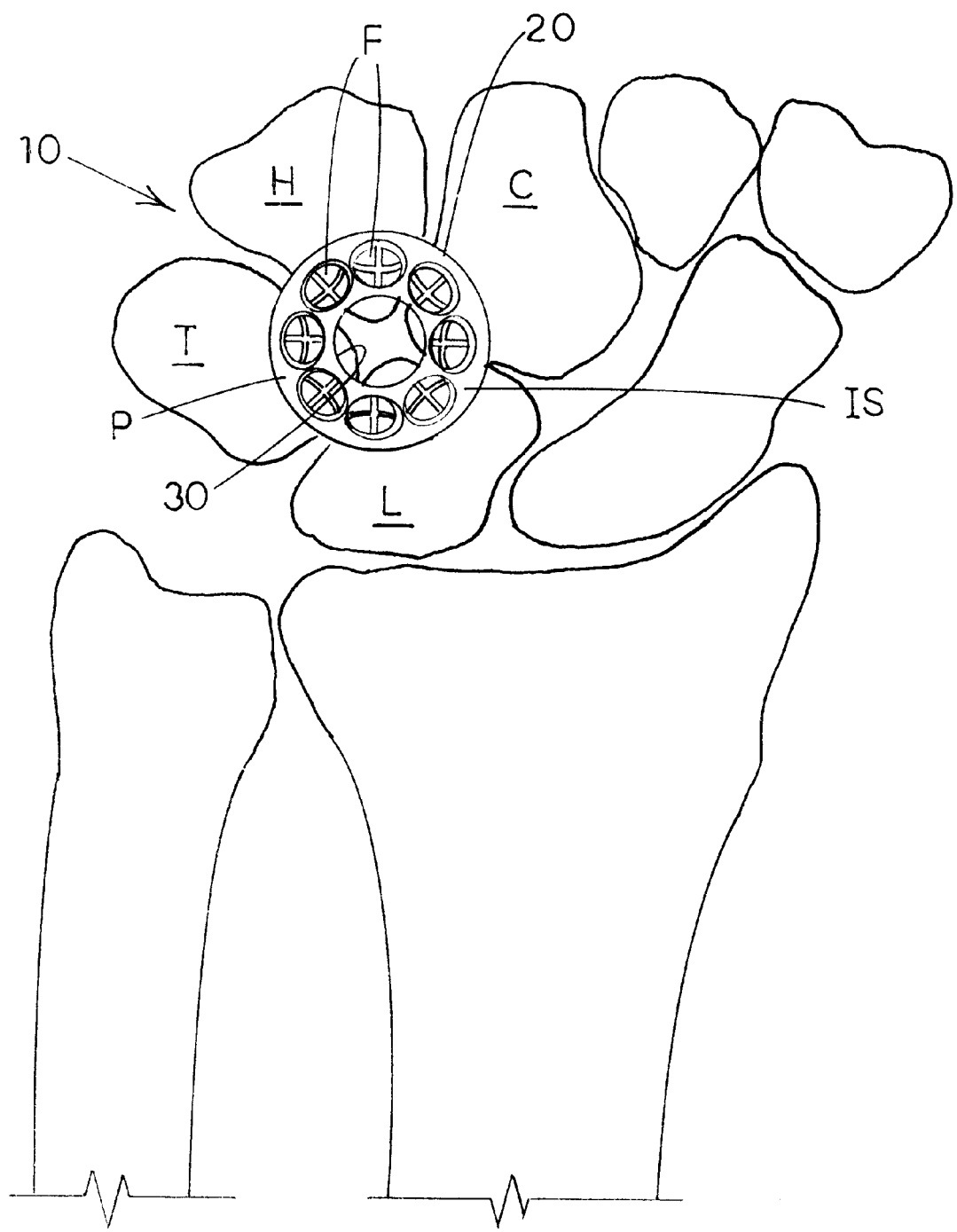
FIG. 1B of the drawings is identical to FIG. 1A but illustrating the bone fusion apparatus according to the present invention secured in place by a plurality of bone screws utilized as fasteners.
Figure 2:
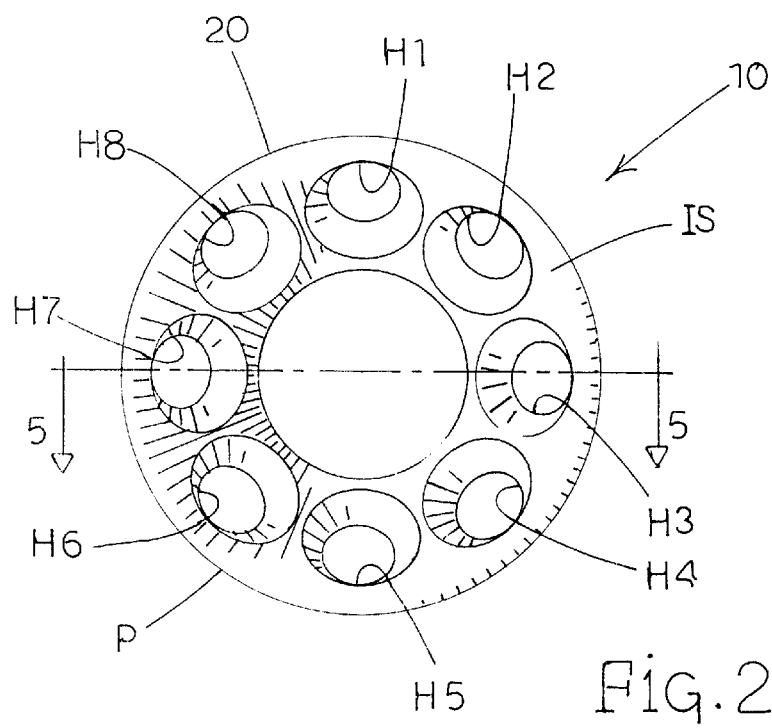
FIG. 2 of the drawings is an isolated top plan view of the bone fusion apparatus according to the present invention.

FIG. 1B of the drawings illustrates plate P fixed in a preferred position for limited wrist fusion with fasteners F shown as bone screws fixed to the underlying bones, which are carpal area bones, through holes H1–H8. Intraoperative fluoroscopic and standard AP and lateral radiographs can be undertaken to ensure appropriate plate P placement and screw fixation. Range of motion testing can be undertaken to ensure excellent stability of the fusion plate. Additional bone graft can be packed within the center portion of the four-corner region through plate P itself without difficulty.

Irrigation and debridement of the wound is undertaken, and sequential repair of the capsule and retinacular structures are undertaken using suitable (#4-0) absorbable sutures. After skin closure, a short-arm light bulky splint is placed allowing early active finger range of motion. Post-operatively after the sutures have been removed at approximately one week, either a removable splint can be placed to allow early range of motion exercises or alternatively, a short-arm cast can be placed for three to four weeks of protection. Radiographs should be taken on a sequential basis to ensure appropriate fusion of the four-corner region prior to allowing return to normal activities.

It can therefore be readily understood by those of skill in the art that bone fusion apparatus 10 can be positioned over and affixed precisely in position against a variety of bones in a variety of anatomical locations, such as, for example, against foot bones, cranial-facial bones, or any other suitable bones in addition to use with wrist bones for total bone fusion or for limited bone fusion as described herein. Bone burr 100 can be used with any suitable bones of any suitable location in a fashion as described with the wrist bones above in order to advantageously provide a precise location in which bone fusion apparatus 10 can at least partially be fitted during affixation. Fixation of plate P in position as described above therefore can, unlike prior art apparatuses and methods for bone positioning and fusion, quite advantageously provide radial compression of bones to be positioned and/or fused wherein the bones are drawn and urged toward one another and toward a vertical axis disposed through plate P at least generally perpendicular to the plane represented by line L1. Fixation of plate P in position as described above also provides desirable stability so as to allow the bones beneath and to which plate P is affixed to fuse properly.

Utilization of plate P for wrist fusion is believed to eliminate complications which can typically occur with the use of conventional bone fusion apparatuses such as wrist fusion plates for limited wrist fusion as primarily for patients with post-traumatic or osteoarthritis. Specifically, the plate is countersunk into the bones being fusion decreasing any contact between the plate and overlying soft tissues and tendons. The plate allows bone graft to be placed even after fixation at the fusion site. The plate and screws form a three axis fixation of the bones being fused with circumferential compression and compression of the plate to the bones. The plate allows screw placement at an oblique angle to the main plane of the plate providing the aforementioned advantages. It is also specifically envisioned according to this invention that bone fusion apparatus 10 can be used simply to position one or more bones relative to one or more other bones or structures regardless of whether fusion of the associated bones is desired.

It can therefore be seen that the present invention provides a novel bone fusion apparatus and method for attaching to a variety of bones for bone fusion. It can also be seen that the present invention provides a bone fusion apparatus and method particularly suitable for utilization in fusing wrist bones with or without attachment to the radius bone or to a metacarpal bone. Finally, it can be understood that the present invention provides a bone fusion apparatus and method wherein the bone fusion apparatus can effectively and easily be positioned and affixed precisely in place and can be effectively and easily utilized for bone fusion with a unique three dimensional fixation method.

It will be understood that various details of the invention can be changed without departing from the scope of the invention. Furthermore, the foregoing description is for the purpose of illustration only, and not for the purpose of limitation, as the present invention is defined by the following, appended claims.

What is claimed is:

1. A bone fusion apparatus for positioning over and attachment to one or more bones, said bone fusion apparatus comprising:

(a) a plate having an outer side for at least partially contacting bone and an opposite inner side, and said plate having a top outer edge of greatest diameter and a smaller diameter, bottom inner edge which defines an at least substantially central opening through said plate;

(b) said plate being substantially conical in shape such that said plate tapers outwardly from said inner edge of said plate to said outer edge of said plate; and (c) said plate defining a plurality of holes therethrough between said inner edge and said outer edge, each of said holes adapted for receiving a bone fastener for attaching said plate to one or more bones whereby the plate and bone fasteners can cause radial compression of the one or more bones.

2. The bone fusion apparatus of claim 1 for wrist bone fusion wherein said plate includes at least four (4) holes configured for simultaneous alignment for attachment of a bone fastener to a lunate bone, a triquetrium bone, a hamate bone, and a capitate bone of a carpus area of a wrist.

3. The bone fusion apparatus of claim 1 wherein said holes are countersunk on said inner side of said plate.

4. The bone fusion apparatus of claim 1 wherein said outer side of said plate is disposed at an angle of between approximately 0 and 90 degrees to a plane on which said central opening of said plate is disposed.

5. The bone fusion apparatus of claim 1 wherein said wrist fusion plate is constructed of stainless steel.

6. The bone fusion apparatus of claim 1 wherein said wrist fusion plate is constructed of a bioabsorbable material.

7. A bone fusion system for precisely positioning and affixing a bone fusion apparatus to a plurality of bones, said bone fusion system comprising:

(a) an annular plate having an outer side for at least partially contacting bone and an opposite inner side, and said plate having a top outer edge of greatest diameter and a smaller diameter, bottom inner edge which defines an at least substantially central opening through said plate;

(b) said plate being substantially conical in shape such that said plate tapers outwardly from said inner edge of said plate to said outer edge of said plate;

(c) said plate defining a plurality of holes therethrough between said inner edge and said outer edge, each of said holes adapted for receiving a bone fastener for attaching said plate to a plurality of bones; and (d) a bone burr for burring away bone in preparation for positioning and affixing said plate, said bone burr being substantially cone-shaped and being threaded on its outer side for burring away bone, and said bone burr having an outer configuration at least generally matching that of said outer side of said plate such that said bone burr can be easily used to burr away bone to create a burred away location in a desired area of bones, and wherein said plate can subsequently be placed and affixed in position in the burred away location.

8. The bone fusion system of claim 7 further comprising a handle adapted for engaging said bone burr for rotating said bone burr to burr away bone.

9. The bone fusion system of claim 8 wherein said handle is "t"-shaped.

10. The bone fusion system of claim 8 wherein said handle is a quick coupling adapter for a power instrument.

11. The bone fusion system of claim 7 wherein said outer threaded side of said bone burr forms a point.

12. A method of affixing a bone fusion apparatus, said method comprising the steps of:

(a) providing a bone fusion apparatus comprising:
(i) an annular plate having an outer side for at least partially contacting bone and an opposite inner side, and said plate having a top outer edge of greatest diameter and a smaller diameter, bottom inner edge which defines an at least substantially central opening through said plate;
(ii) said plate being substantially conical in shape such that said plate tapers outwardly from said inner edge of said plate to said outer edge of said plate; and
(iii) said plate defining a plurality of holes therethrough between said inner edge and said outer edge, each of said holes adapted for receiving a bone fastener for attaching said plate to bone;

(b) positioning said bone fusion apparatus over a desired bone area; and (c) affixing said bone fusion apparatus to one or more bones of said bone area wherein said bone fusion apparatus causes radial compression of the one or more bones to which said bone fusion apparatus is affixed.

13. The method of claim 12 wherein said plate of said bone fusion apparatus is for wrist fusion and wherein said bone fusion apparatus is positioned such that at least one hole is positioned for attachment of a bone fastener to each of a lunate bone, a triquetrium bone, a hamate bone, and a capitate bone of a carpus area.

14. The method of claim 13 wherein said plate is affixed at least to said lunate bone, triquetrium bone, hamate bone, and capitate bone of the carpus area.

15. The method of claim 14 wherein said plate is affixed to said lunate bone, triquetrium bone, hamate bone, and capitate bone of the carpus area by fastening a bone screw through a plurality of holes of said plate.

16. The method of claim 13 further comprising a step prior to the step of paragraph (c) of burring away bone to create a burred away area at a desired placement location for said bone fusion apparatus to be positioned and affixed, and further comprising placing said plate at least partially in said burred away area and affixing said plate in position with minimal or no slippage of said plate as said plate is affixed.

17. A method of affixing a bone fusion apparatus, said method comprising the steps of:

(a) providing a bone fusion system comprising:
(i) an annular plate having an outer side for at least partially contacting bone and an opposite inner side, and said plate having a top outer edge of greatest diameter and a smaller diameter, bottom inner edge which defines an at least substantially central opening through said plate;
(ii) said plate being substantially conical in shape such that said plate tapers outwardly from said inner edge of said plate to said outer edge of said plate;
(iii) said plate defining a plurality of holes therethrough between said inner edge and said outer edge, each of said holes adapted for receiving a bone fastener for attaching said plate to bone; and
(iv) a bone burr for burring away bone in preparation for positioning and affixing said plate, said bone burr being substantially cone-shaped and being threaded on its outer side for burring away bone and said bone burr having an outer configuration at least generally matching that of said outer side of said plate such that said bone burr can be easily used to burr away bone in a desired area to create a burred away location, and wherein said plate can subsequently be placed in the burred away location and affixed there in position;

(b) burring away bone using said bone burr to create a burred away area in a desired location for positioning and affixing said plate;

(c) positioning said plate at least partially in said burred away area with said outer side of said plate positioned adjacent or in contact with one or more bones; and (d) affixing said plate in position while said plate is positioned at least partially in said burred away area by fastening bone screws to said one or more bones through one or more of said holes of said plate.

18. The method of claim 17 wherein burring away bone using said bone burr comprises rotating a handle attached to said bone burr to rotate said bone burr.

19. A method of affixing a bone fusion apparatus for wrist fusion, said method comprising the steps of:

(a) providing a bone fusion system comprising:
   (i) an annular plate having an outer side for at least partially contacting bone and an opposite inner side, and said plate having a top outer edge of greatest diameter and a smaller diameter, bottom inner edge which defines an at least substantially central opening through said plate;
   (ii) said plate being substantially conical in shape such that said plate tapers outwardly from said inner edge of said plate to said outer edge of said plate;
   (iii) said plate defining a plurality of holes therethrough between said inner edge and said outer edge, each of said holes adapted for receiving a bone fastener for attaching said plate to bone; and
   (iv) a bone burr for burring away bone in preparation for positioning and affixing said plate, said bone burr being substantially cone-shaped and being threaded on its outer side for burring away bone and said bone burr having an outer configuration at least generally matching that of said outer side of said plate such that said bone burr can be easily used to burr away bone in a desired area to create a burred away location, and wherein said plate can subsequently be placed in the burred away location and affixed there in position;

(b) burring away bone using said bone burr to create a burred away area in a carpus area of a wrist for positioning and affixing said plate;

(c) positioning said plate at least partially in said burred away area with said at least one of said holes of said plate being in simultaneous alignment for attachment of a bone fastener to a lunate bone, a triquetrium bone, a hamate bone, and a capitate bone of the carpus area; and (d) affixing said plate in position while said plate is positioned at least partially in said burred away area by fastening bone screws to said lunate bone, triquetrium bone, hamate bone, and capitate bone through one or more of said holes of said plate.

* * * * *